United States Patent
Matta et al.

(10) Patent No.: US 10,426,854 B2
(45) Date of Patent: Oct. 1, 2019

(54) APPARATUS AND METHOD TO MAKE HIGH LEVEL DISINFECTANT

(71) Applicant: Medivators Inc., Minneapolis, MN (US)

(72) Inventors: John Matta, Shoreview, MN (US); Huyen Bui, Brooklyn Park, MN (US); Tuan Nguyen, Chaska, MN (US)

(73) Assignee: Medivators Inc., Minneapolis, MN (US)

( * ) Notice: Subject to any disclaimer, the term of this patent is extended or adjusted under 35 U.S.C. 154(b) by 0 days.

(21) Appl. No.: 16/337,006

(22) PCT Filed: Sep. 28, 2017

(86) PCT No.: PCT/US2017/053934
§ 371 (c)(1),
(2) Date: Mar. 27, 2019

(87) PCT Pub. No.: WO2018/064291
PCT Pub. Date: Apr. 5, 2018

(65) Prior Publication Data
US 2019/0216961 A1    Jul. 18, 2019

Related U.S. Application Data

(60) Provisional application No. 62/400,774, filed on Sep. 28, 2016, provisional application No. 62/452,666, filed on Jan. 31, 2017.

(51) Int. Cl.
*A61L 2/18*  (2006.01)
*B01J 19/18* (2006.01)
*B01J 16/00* (2006.01)

(52) U.S. Cl.
CPC ........... *A61L 2/186* (2013.01); *B01J 19/1862* (2013.01); *A61L 2202/11* (2013.01);
(Continued)

(58) Field of Classification Search
CPC .. A61L 2/186; A61L 2202/24; A61L 2202/11; B01J 19/1862; B01J 2219/00281;
(Continued)

(56) References Cited

U.S. PATENT DOCUMENTS 5,116,575 A    5/1992  Badertscher et al.
5,350,563 A    9/1994  Kralovic et al.
(Continued)

FOREIGN PATENT DOCUMENTS

CA    2569025    6/2008
CN    1128257    8/1996
(Continued)

OTHER PUBLICATIONS

International Preliminary Report on Patentability issued in PCT/US2017/053934, dated Apr. 11, 2019.
(Continued)

*Primary Examiner* — Lessanework Seifu

(57) ABSTRACT

Apparatuses, devices and methods for creating a high level disinfectant, comprising peracetic acid for disinfecting medical devices are disclosed. The peracetic acid solution is made from a reaction of tetraacetylethylenecUamine powder, sodium percarbonate, and citric acid moHohydrate in water.

19 Claims, 2 Drawing Sheets

(52) U.S. Cl.
CPC ............ *A61L 2202/24* (2013.01); *B01J 16/00* (2013.01); *B01J 2219/0059* (2013.01); *B01J 2219/0072* (2013.01); *B01J 2219/00281* (2013.01)

(58) Field of Classification Search
CPC ........ B01J 2219/0072; B01J 2219/0059; B01J 16/00
See application file for complete search history.

(56) References Cited

U.S. PATENT DOCUMENTS

| | | |
|---|---|---|
| 7,235,252 B2 | 6/2007 | Preto et al. |
| 8,920,715 B2 | 12/2014 | Roberts et al. |
| 9,701,931 B2 | 7/2017 | Moore |
| 2002/0182103 A1 | 12/2002 | Biering et al. |
| 2005/0153854 A1 | 7/2005 | Meyer et al. |
| 2007/0184999 A1 | 8/2007 | DiCosimo et al. |
| 2009/0142235 A1 | 6/2009 | Rico et al. |
| 2011/0293472 A1 | 12/2011 | McSherry et al. |
| 2012/0108878 A1 | 5/2012 | Conrad |
| 2016/0286800 A1 | 10/2016 | Dagher et al. |

FOREIGN PATENT DOCUMENTS

| | | |
|---|---|---|
| CN | 104479888 | 4/2015 |
| GB | 2522074 | 7/2015 |
| WO | 2016055773 A1 | 4/2016 |
| WO | 2016082897 A1 | 6/2016 |

OTHER PUBLICATIONS

International Preliminary Report on Patentability issued in PCT/US2017/053932, dated Apr. 11, 2019.
International Search Report and Written Opinion of the International Searching Authority dated Dec. 11, 2017, of International PCT Application No. PCT/US2017/053932 filed Sep. 28, 2017.
International Search Report and Written Opinion of the International Searching Authority dated Dec. 12, 2017, of International PCT Application No. PCT/US2017/053934 filed Sep. 28, 2017.

APPARATUS AND METHOD TO MAKE HIGH LEVEL DISINFECTANT

CROSS REFERENCE TO RELATED APPLICATIONS

This application claims priority to U.S. Provisional Patent Application Ser. No. 62/400,774 filed Sep. 28, 2016 and also claims priority to U.S. Provisional Patent Application Ser. No. 62/452,666 filed Jan. 31, 2017. These applications are incorporated herein by reference, in their entireties.

TECHNICAL FIELD

Embodiments of the present disclosure relate to disinfectant solutions. More specifically, embodiments of the present disclosure relate to producing disinfectant solutions from solid chemistries, which are used for disinfecting a medical device.

BACKGROUND

Many medical devices and instruments may be reused on a number of patients. Before a medical device or instrument is used on another patient, the medical device or instrument generally needs to be reprocessed. For example, after an endoscope is used on a patient, a number of steps are required to reprocess the endoscope before that the endoscope can be reused. Included in the steps of reprocessing an endoscope is a disinfecting step using, for example, a liquid disinfectant solution.

Conventionally, liquid disinfectant solutions are prepared as aqueous solutions and are then shipped by a manufacturer to a hospital or other facility. The disinfectant solutions may be shipped as a concentrate which is then diluted at the hospital or other facility to disinfect an endoscope. Alternatively, the disinfectant solutions may be shipped end-user concentrations and then used "as is" for disinfecting. For either the concentrated or the "as is" disinfectant solution most of the shipping cost is due to the water in the solution, not the needed disinfectant.

Apparatus and devices designed for the at least partially automated cleaning and sterilization of medical devices and instruments are known. Antimicrobial solutions adapted for use in such sterilizing devices are also known, but may suffer drawbacks either in terms of storage, handling, corrosiveness, or compromised capability of rapid in situ dissolution of the medical device or instrument.

Some of these antimicrobial solutions use peracetic acid or other strong oxidants as a sterilizing agent. Storage conditions which may subject a contained peracetic acid solution to increases in temperature must be avoided, and storage of containers which vent such solutions into the atmosphere may be problematic and subject to regulatory restrictions.

There is a need for improved high level antimicrobial and disinfectant solutions and systems to clean and sterilize medical devices and instruments that do not suffer from any of the problems associated with previous solutions and systems.

SUMMARY

Representative embodiments of the present disclosure are related to apparatus and methods for producing and using antimicrobial and disinfectant solutions for use with cleaning and sterilizing medical devices and instruments.

In one aspect, the invention is directed to an apparatus to make a peracetic acid high level disinfectant solution. The apparatus includes a solid dispensing system, a water source, two reactor chambers, and a storage reservoir. A solid dispensing system has a bulk dispenser for solid tetraacetylethylenediamine (TAED), a bulk dispensing system for solid sodium percarbonate and a bulk dispensing system for solid citric acid monohydrate. A heated water delivery system is provided to add heated water to the reactor chambers and storage reservoir. A first reactor chamber is used to mix the solid TAED and sodium percarbonate with heated water to provide a peracetic acid solution. A conduit is provided to deliver heated water from the heated water system to the first reactor chamber. A second reactor chamber mixes the peracetic acid solution with a weak organic acid, such as citric acid monohydrate, to provide a pH controlled peracetic acid solution. A conduit delivers the peracetic acid solution from the first reactor chamber to the second reactor chamber. A storage reservoir dilutes the pH controlled peracetic acid solution with water to provide a peracetic acid high level disinfectant solution. A conduit delivers the pH controlled peracetic acid solution from the second reactor chamber to the storage reservoir, and a conduit delivers water to the storage reservoir.

The apparatus may comprise a water delivery system having a pump to deliver heated water to the first reactor chamber. The heated delivery system may deliver water to the first reactor chamber at a temperature of from about 30-50° C. For example, water may be delivered to the first reactor chamber at a temperature of about 40° C.

The first reactor chamber may comprise a mixer. The mixer may comprise a rotary mixing blade or other high shear blade. Other mixing blades may comprise swift mixing blades, western mixing blades, egg beater blades, impeller blades or mud buster blades. The first reactor chamber may be capable of mixing the water, solid TAED, and solid sodium percarbonate for a period of time, such as about one minute.

A conduit may deliver peracetic acid solution from the first reactor chamber to the second reactor chamber and also may include a filter to prevent the transfer of undissolved solids to the second reactor chamber. A filter may be made from known materials including polymers, such as polytetrafluoroethylene, polypropylene, nylon or polyethylene. Alternative filter materials include metal, glass, or ceramic.

Another conduit may deliver pH controlled peracetic acid from the second rector chamber to the storage reservoir and may include a filter to prevent transfer of undissolved solids.

The water used to dilute the pH controlled peracetic acid may be delivered at a temperature of about 18 to about 40° C., more specifically, about 25 to about 40° C.

The peracetic acid high level disinfectant solution is at a temperature of about 20-40° C. For example, the solution may be at a temperature of about 30° C. The peracetic acid has a pH of from about 5-7, for example a pH of about 6, a peracetic acid concentration of about 1200-2200 ppm, more specifically, about 1200-2000 ppm, and a hydrogen peroxide concentration of less than about 500 ppm.

In another aspect, the invention is directed to a method of making a peracetic acid high level disinfectant solution. The method includes: (i) dispensing a solid mixture of TAED and sodium percarbonate from a bulk container into a first reactor chamber, (ii) adding heated water to the first reactor chamber, (iii) mixing the heated water, TAED and sodium percarbonate to form a peracetic acid solution, (iv) dispensing solid citric acid monohydrate from a bulk container into a second reactor chamber, (v) adding the mixed peracetic acid solution to the second reactor chamber to provide a pH controlled peracetic acid solution, (vi) adding the pH controlled solution to a storage reservoir, and (vii) diluting the pH controlled peracetic acid solution with water in the storage reservoir to provide the peracetic acid high level disinfectant solution.

The heated water may be pumped into the first reactor chamber. The heated water may be at a temperature of from about 30° C. to about 50° C., for example at a temperature of about 40° C.

The heated water, solid TAED, and solid sodium percarbonate are mixed in the first reactor chamber by a mixer. The mixer may comprise a rotary mixing blade, a swift mixing blade, a western mixing blade, an egg beater blade, or a mud buster blade. The heated water, TAED, and sodium percarbonate are mixed in the first reactor chamber for a period of time, such as about one minute, to form the peracetic acid solution.

The peracetic acid solution is then pumped into the second reactor chamber. The peracetic acid may be filtered to prevent transfer of undissolved solids into the second reactor chamber. The pH controlled peracetic acid may also be filtered to prevent transfer of undissolved solids into the storage reservoir.

The water used to dilute the pH controlled peracetic acid in the storage reservoir is at a temperature of about 18 to about 40° C., more specifically, about 25 to about 40° C.

The peracetic acid high level disinfectant solution is at a temperature in the range of from about 20° C. to about 40° C., for example 30° C., has a pH in the range of from about 5-7, for example a pH about 6, a peracetic acid concentration of about 1200-2200 ppm, more specifically, about 1200-2000 ppm, and a hydrogen peroxide concentration of less than about 500 ppm.

The peracetic acid high level disinfectant solution as described above may be used to clean and disinfect reusable medical apparatus and equipment, for example a dialysis machine.

The peracetic acid high level disinfectant solution as described above may be used in an automated endoscopic reprocessing system (AER system).

While multiple embodiments are disclosed, still other embodiments of the present disclosure will become apparent to those skilled in the art from the following detailed description and claims, which shows and describes illustrative embodiments of the disclosure. Accordingly, the drawings and detailed description are to be regarded as illustrative in nature and not restrictive.

DETAILED DESCRIPTION OF THE DRAWINGS

Figure 1:
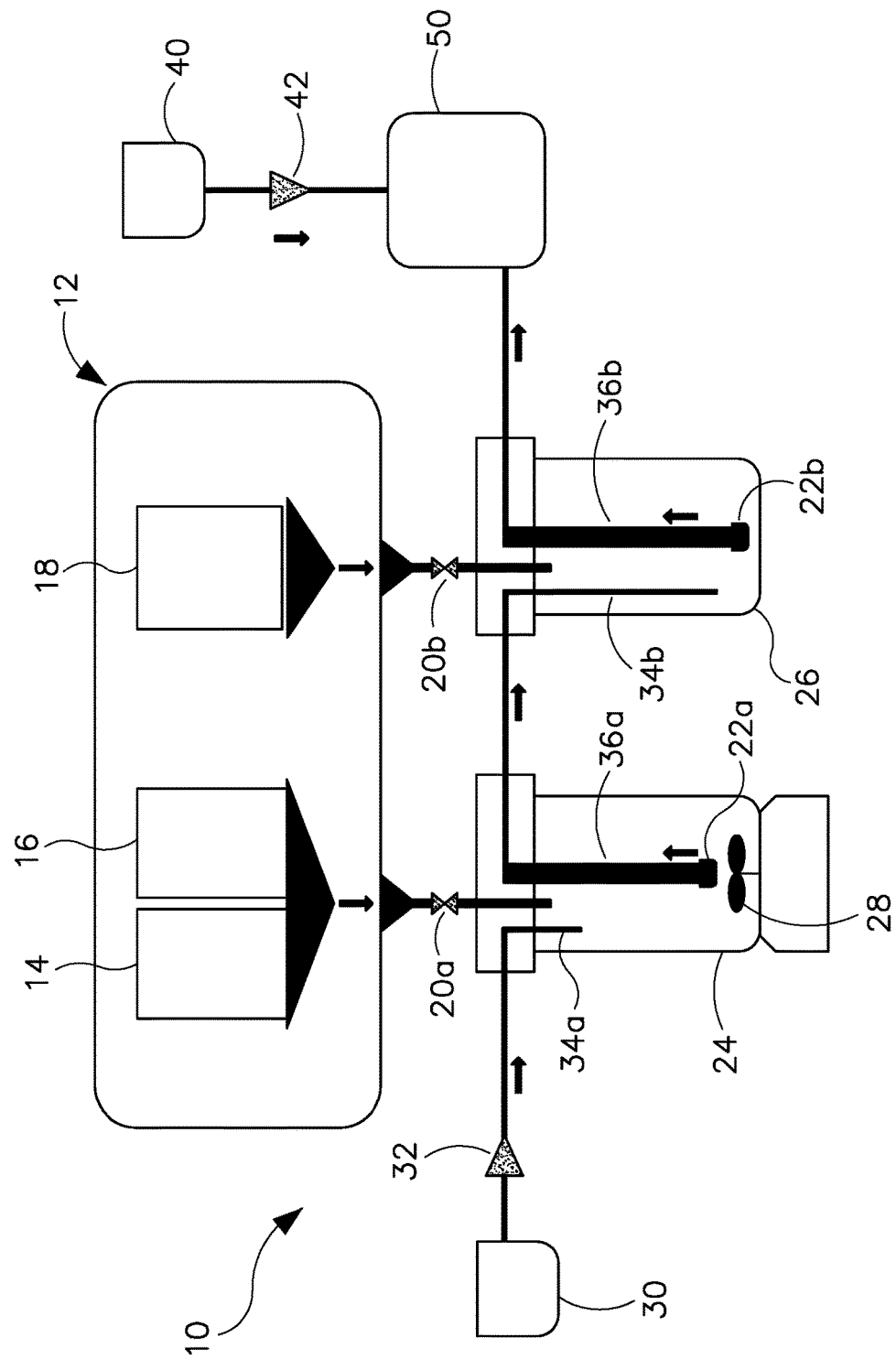
FIG. 1 illustrates an exemplary embodiment of an apparatus to make a high level disinfectant.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present application. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the application are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of this application, examples of which are illustrated in the accompanying drawings. While the application will be described in conjunction with the illustrated embodiments, it will be understood that they are not intended to limit the application to those embodiments. On the contrary, the application is intended to cover all alternatives, modifications, and equivalents that may be included within the application as defined by the appended claims.

It is noted that, as used in this specification and the appended claims, the singular forms "a," "an" and "the" include plural referents unless expressly and unequivocally limited to one referent. Thus, for example, reference to "a filter" includes one, two, three or more filters.

We refer now to the drawings wherein depicted elements are not necessarily shown to scale and wherein like or similar elements are designated by the same reference numeral through the several views.

Referring to the drawings in general, it will be understood that the illustrations are for the purpose of describing particular embodiments of the disclosure and are not intended to be limiting thereto.

While most of the terms used herein will be recognizable to those of ordinary skill in the art, it should be understood that when not explicitly defined, terms should be interpreted as adopting a meaning presently accepted by those of ordinary skill in the art.

Peracetic acid (PAA), also referred to as peroxyacetic acid, may be produced by the reaction of acetic acid and hydrogen peroxide in an aqueous solution. The PAA is a high level disinfectant for cleaning, disinfecting and sterilizing medical devices and instruments. TAED as a solid powder is used to react in solution with a solid source of peroxide such as sodium percarbonate or sodium perborate to generate peracetic acid. When sodium percarbonate dissolves in water, hydrogen peroxide is generated. At elevated temperatures, for example 30° C. or higher, TAED will quickly react with hydrogen peroxide in a first reaction to generate PAA and triacetylethylenediamine and then react with additional hydrogen peroxide to generate peracetic acid and diacetylethylenediamine. When the reaction is complete, the solution obtained has a pH that may be greater than 8.0. In order for PAA to be effective and stable, the pH is lowered to about 6.0 by adding citric acid monohydrate. The preferred peracetic acid high level disinfectant solution has a pH of between about 5 to about 7, more specifically, between about 5.5 to about 6.5, and more specifically, about 6.0, at a concentration of 1200-2200 ppm, more specifically, about 1200-2000 ppm, and more specifically between about 1700-1900, ppm PAA and about 200-500 ppm $H_2O_2$. In another embodiment, the peracetic acid high level disinfectant solution has an $H_2O_2$ concentration of less than 500 ppm, more specifically, less than 300 ppm. The peracetic acid high level disinfectant solution is effective as a microbiocidal and disinfectant, and has low corrosive properties.

FIG. 1 illustrates an example of a peracetic acid mixing system 10 to provide a peracetic acid high level disinfectant solution. Mixing system 10 comprises a solid dispensing system 12, a first reactor chamber 24, a second reactor chamber 26, and a storage reservoir or chamber 50.

Solid dispensing system 12 comprises a bulk container of TAED 14, a bulk container of sodium percarbonate 16, and a bulk container of a weak organic acid, such as citric acid monohydrate 18. The solid dispensing system 12 maintains the solids as powders separate from each other until mixing is desired. These components are provided in powder form in two or more bulk containers with the reactive components (TAED and sodium percarbonate, and) in one or more bulk containers, and citric acid monohydrate powder for pH adjustment in another bulk container. In a preferred configuration each component is maintained separately from each other. These components are dispensed into the first and second reactors after going through solid dispensing access points 20a, 20b.

In a representative embodiment, approximately 1.66 kg of TAED is contained in the solid dispensing system 12, which is enough TAED to make about 50 batches or cycles of 10 liters of high level disinfectant solution. Approximately 2.08 kg of sodium percarbonate is contained in the solid dispensing system 12, which is enough to make about 50 batches or cycles of 10 liters of high level disinfectant solution. In a single batch or cycle, about 33.2 g of TAED and about 41.5 g of sodium percarbonate is dispensed through the solid dispensing access point 20a. In addition, approximately 1.50 kg of citric acid monohydrate is contained in the solid dispensing system 12, which is enough for about 50 batches or cycles of 10 liters of high level disinfectant solution. In a single cycle, about 30 g of a weak organic acid, such as citric acid monohydrate, is dispensed into solid dispensing access point 20b.

In another representative embodiment, approximately 0.83 kg of TAED is contained in the solid dispensing system 12, which is enough TAED to make about 50 batches or cycles of 5 liters of high level disinfectant solution. Approximately 1.04 kg of sodium percarbonate is contained in the solid dispensing system 12, which is enough to make about 50 batches or cycles of 5 liters of high level disinfectant solution. In a single batch or cycle, about 16.6 g of TAED and about 20.1.7 g of sodium percarbonate is dispensed through the solid dispensing access point 20a. In addition, approximately 0.75 kg of citric acid monohydrate is contained in the solid dispensing system 12, which is enough for about 50 batches or cycles of 5 liters of high level disinfectant solution. In a single cycle, about 15 g of a weak organic acid, such as citric acid monohydrate, is dispensed into solid dispensing access point 20h.

The TAED and sodium percarbonate are mixed with water in the first reactor chamber 24, using mixer 28. Water is pumped from water source 30, which heats about 2.0 liters of water (for a 10 liter batch) to a temperature of from about 35-45° C., for example about 40° C., through inlet tube 34a into first reactor chamber 24. A 5 liter batch would require about 1.0 to about 1.5 liters of water to be heated to a temperature of from about 35-45° C., for example about 40° C. The water is pumped with pump 32 to first reactor chamber 24 at an optional flow rate of about 4.5-6.1 liters per minute (1.2-1.6 gallons per minute), for example about 5.3 liters per minute (1.4 gallons per minute) while maintaining the water at a temperature of about 40° C. Mixer 28 facilitates TAED and sodium percarbonate to dissolve in water and react to create a PAA solution. The initial pH of the PAA solution is about 8. In one embodiment, a filter or mesh 22a is located within first reactor chamber 24 around outlet tube 36a to filter any undissolved solids and prevent these materials from passing through outlet tune 36a and into second reactor chamber 26.

In one embodiment, the first reactor chamber 24 can be sized at about 3 liters for a 10 liter batch of high level disinfectant solution, or about can be less than 2 liters for a 5 liter batch of high level disinfectant solution. In another embodiment, the second reactor chamber 26 is also sized at about 3 liters for a 10 liter batch of high level disinfectant solution or less than 2 liters for a 5 liter batch of high level disinfectant solution. The first and second reactor chambers may be made from materials such as plastic, metal, or tempered glass. First reactor chamber 24 and second reactor chamber 26 may be insulated to maintain a desired temperature. For example, first reactor chamber 24 and second reactor chamber 26 may have a heat jacket, or an internal heater.

A weak organic acid, such as citric acid monohydrate is added to second reactor chamber 26 through solid dispensing access point 20b from the bulk container 18. PAA created in first reactor chamber 24 is added to second reactor chamber 26 via a conduit comprising outlet tube 36a and inlet tube 34b at an optional flow rate of about 4.5-6.1 liters per minute (1.2-1.6 gallons per minute), for example 5.3 liters per minute (1.4 gallons per minute). Mixing of citric acid monohydrate and PAA is effected using the flow of the incoming PAA solution. The citric acid monohydrate is used to lower the pH of the PAA solution to between about 5 to about 7, specifically, about 6.0.

In one embodiment, the acidified PAA solution is then removed from second reactor chamber 26 through filter or mesh 22b and associated outlet tube 36b. Filter or mesh 22h filters any undissolved solids from the solution. In one embodiment, the acidified PAA solution is removed, at an optional flow rate of about 4.5-6.1 liters per minute (1.2-1.6 gallons per minute), for example about 5.3 liters per minute (1.4 gallons per minute), with a temperature of from about 20-40° C., for example, about 30° C. The acidified PAA solution is transferred to storage reservoir or chamber 50 via a conduit comprising outlet tube 36b. Water (in one embodiment, about 8 liters) from water source 40 is kept at a temperature of about 25-30° C. and is pumped to storage reservoir or chamber 50 using pump 42, In one embodiment the water is pumped at a flow rate of about 1.2-1.6 gallons per minute, for example from about 1.2-1.6 gallons per minute, for example, about 1.4 gallons per minute. In one embodiment, storage reservoir chamber 50 is sized at about 50 liters, and is made from materials selected from plastic, metal, or glass with plastic being preferred. In one embodiment, storage reservoir or chamber 50 comprises about 4-12 liters, preferably about 10 liters of the high level disinfectant solution at a temperature of about 30-40° C. with a concentration of PAA from about 1200-2200 ppm, more specifically, about 1200-2000 ppm, and a hydrogen peroxide concentration of less than about 500 ppm, more specifically, less than 300 ppm, and a pH of from about 5.0 to about 7.0.

For example, 10 liters of a high level disinfectant solution may be present at a concentration of about 1200-2200 ppm, more specifically, about 1200-2000 ppm, and more specifically about 1700-1900 ppm PAA at a temperature of about 30° C., with a pH of about 6.

Another representative embodiment is a method of using the apparatus 10 to make a high level disinfectant solution. The method includes the following steps. Solid TAED and sodium percarbonate, contained in bulk containers 14, 16 as powders, are dispensed by the dispensing system 12 to the first reactor chamber 24. A weak organic acid, such as citric acid monohydrate is dispensed from bulk container 18 to second reactor chamber 26. A water source 30 is allowed to heat an amount of water, such as about 2 liters, to a desired temperature, such as from about 35-45° C., for example, to a temperature of about 40° C., Next, an amount of water, such as about 8.0 liters, at room temperature (25-30° C.) is added to the storage reservoir 50 from water source 40. A first pump 32 is turned on to pump the heated water to the first reactor chamber 24. The pump 32 can then be turned off once all the water has been added. The access point can also closed at this time. The mixer 28 in the first reactor chamber 26 is turned on and allowed to mix the water, TAED and sodium percarbonate solution for a period of time, such as about one minute. Alternatively, a mixing time of 30 seconds to two minutes may be used. After the desired mixing time, the pump is turned on to allow the resulting PAA solution to go through to the second reactor chamber 26 to mix with the citric acid monohydrate, and then finally into the storage reservoir 50 to make the final peracetic acid solution for use as high level disinfectant.

In one embodiment, mixing system 10 may dispense TAED 14, sodium percarbonate 16, and citric acid monohydrate 18 by directly weighing out the mass of each component and dispensing the correct amount into the reactor using the solid dispensing access point 20a, 20b. Alternatively, the correct amount of each component may be packaged into separate disposable bags that can be placed into the proper reactor chamber without the need to pour the solid directly into the reactor chamber. The disposable bags may be made from polyvinyl alcohol, high-density polyethylene fibers, or similar material. The disposable bags may also be dissolvable in water. A dissolvable bag may be made from materials such as polyvinyl alcohol, polylactic acid, or other know nontoxic water-soluble biodegradable polymers. The dissolution rate of the bag may be dependent on the temperature of the water. For example, the bag may dissolve faster in water having a higher temperature. The disposable bags could be added directly to the appropriate reactor chamber without adversely affecting the final high level disinfectant solution.

In an alternative embodiment, TAED 14 and sodium percarbonate 16 may be packaged together in a single disposable bag. The hag may also be dissolvable. Such a bag may allow powders to be premixed, or the bag may have a divider to keep the powders separate until added to the reactor chamber 24. Upon adding water as a liquid source, the divider may dissolve and allow the two powders to mix and react.

In an alternative method, water source 30 may heat an amount of water, such as about 0.8 liters, to a temperature of about 55-65° C., for example, to a temperature of about 60° C. The solid components are dispensed from their respective chambers, allowing the water source to reach the desired temperature before dispensing the water into the first reactor chamber 24. An amount of water, such as about 3.2 liters, in water source 40 is heated or maintained at room temperature (about 20-25° C.). Vent (not shown) in first reactor chamber 24 is opened and pump 32 is turned on. Once the first reactor chamber 24 is filled with water, pump 32 is turned off and the vent is closed. Mixer 28 is turned on for a period of time, such as about 1 minute. Alternatively, contents may be mixed for about 30 seconds or up to two minutes. After mixing, pump 32 is turned on to move the PAA solution to second reactor chamber 26. Citric acid monohydrate 18 is added to second reactor chamber 26 and allowed to mix before the acidified peracetic acid solution is pumped into storage reservoir or chamber 50.

Mixing system 10 is advantageous because the amount of components required for the final high level disinfectant product is reduced when compared to similar processes. The high level disinfectant solution is able to be obtained at a lower temperature, such as 30-35° C. The mixing system 10 is also cleaner because the solids are dissolved into solution during the mixing process, which requires less cleaning.

The high level disinfectant solution comprises little to no acetic acid and is stable for at least 12 hours, and preferably stable for up to four days.

Figure 2:
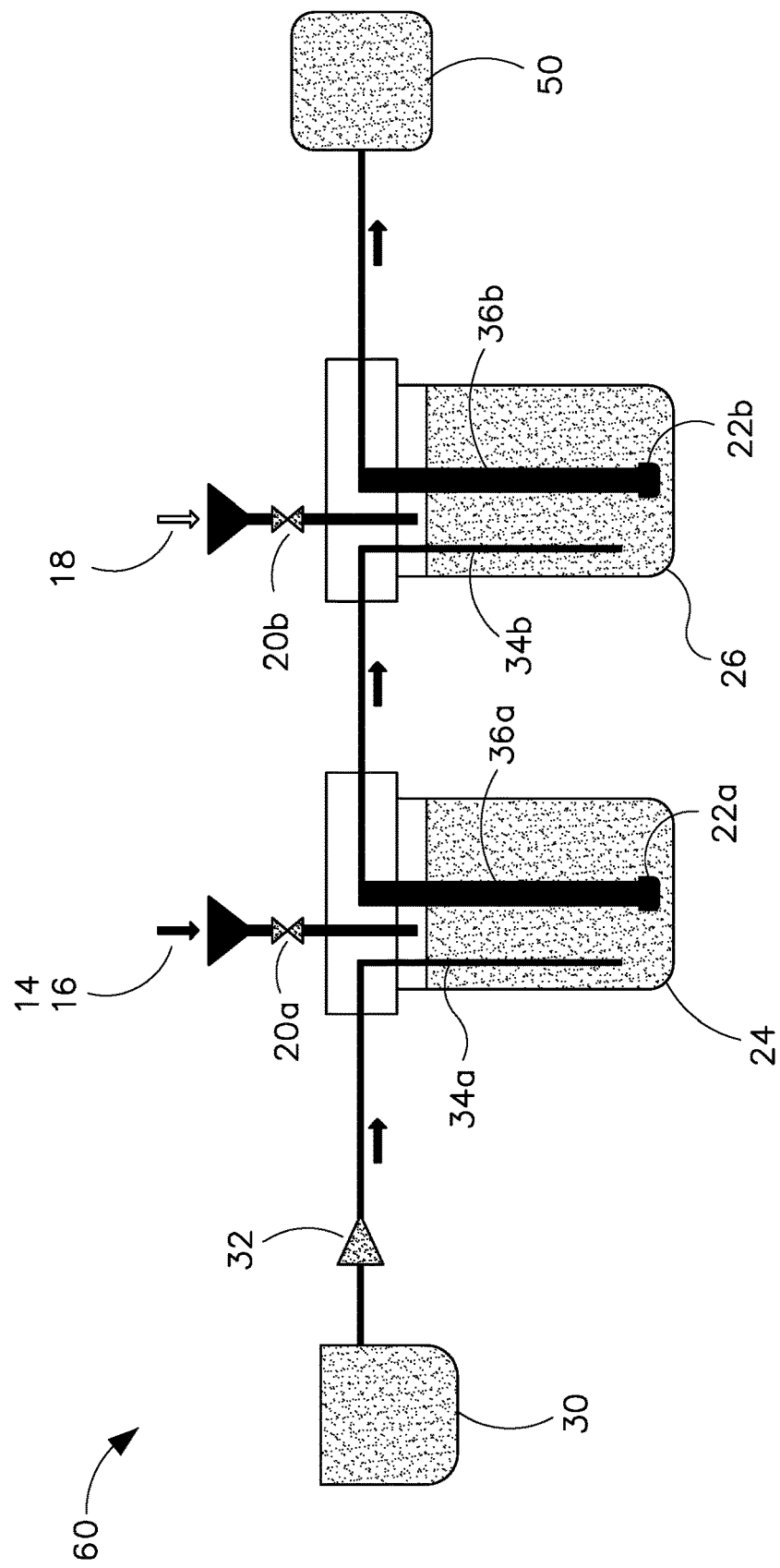
FIG. 2 illustrates an alternative embodiment of an apparatus to make a high level disinfectant.

Another representative embodiment of a mixing system is a continuous flow system as illustrated in FIG. 2. Continuous flow system 60 comprises a first reactor chamber 24, a second reactor chamber 26, and a storage reservoir or chamber 50.

Continuous flow system 60 comprises a TAED 14 addition source, a sodium percarbonate 16 addition source, and a citric acid monohydrate 18 addition source. These components may be provided in powder form in a multi-compartment package with the reactive composition (TAED and sodium percarbonate) in one or more compartments and the pH adjustment powder 18 in another compartment. These components are mixed together when going in to water through solid dispensing access point 20a, 20b.

Continuous flow system 60 may dispense TAED 14, sodium percarbonate 16, and citric acid monohydrate 18 by directly weighing out the mass of each component and dispense the correct amount into the reactor using the solid dispensing access point.

Alternatively, the correct amount of each component may be packaged into separate disposable bags that can be placed into the proper reactor chamber without the need to pour the solid directly into the reactor chamber. The disposable bags may be made from polyvinyl alcohol, high-density polyethylene fibers, or similar material. The disposable bags may also be dissolvable in water. A disposable bag may be made from a material selected from polyvinyl alcohol, polylactic acid, or other know nontoxic water-soluble biodegradable polymers. The dissolution rate may be dependent on the temperature of the water. For example, the bag may dissolve faster in water at a higher temperature. The disposable bags could be added directly to the appropriate reactor chamber without adversely affecting the final solution.

In an alternative embodiment, TAED 14 and sodium percarbonate 16 may be packaged together in a single disposable bag. The bag may be dissolvable. Such a bag may allow powders to be premixed, or the bag may have a divider to keep the powders separate until added to the reactor chamber 24. Upon adding water as a liquid source, the divider may dissolve and allows the powders to mix.

In a representative embodiment, approximately 23.3 g of TAED and about 16.6 g of sodium percarbonate is dispensed through the solid dispensing access point 20a. Approximately 16.6 g of citric acid monohydrate is dispensed through solid dispensing access point 20b. Optionally, approximately 0.08 g of a surfactant, for example, Fluronic F68 LF (Sigma-Aldrich, St. Louis, Mo.) is also added. Other known surfactants may also be used together with or in place of Pluronic F68 LF.

First reactor chamber 24 mixes solid TAED and sodium percarbonate with water. Water is added from water source 30, which heats an amount of water, such as about 4.0 liters, to a temperature of from about 55-80° C. or higher, for example at a temperature of about 60° C. The water is pumped with pump 32 to first reactor chamber 24 at a flow rate, such as from about 4.5-6.1 liters per minute (1.2-1.6 gallons per minute), for example 5.3 liters per minute (1.4 gallons per minute) while maintaining a temperature of about 35.45° C., for example, at temperature of about 40° C. or higher. Mixer 28 facilitates TAED and sodium percarbonate to dissolve in water and react to create a PAA solution. In an embodiment, filter and mesh 22a is located within first reactor chamber 24 to filter any undissolved solids from passing to second reactor chamber 26. Filters or meshes 22a, 22h may be made from materials selected from polytetrafluoroethylene, polyethylene, or nylon.

Citric acid monohydrate 18 is added to second reactor chamber 26 through solid dispensing access point 20b. PAA created in first reactor chamber 24 is added to second reactor chamber 26 at a flow rate, such as from about 4.5-6.1 liters per minute (1.2-1.6 gallons per minute), for example, about 5.3 liters per minute (1.4 gallons per minute) with a pH of greater than or equal to about 8.0. Mixing of citric acid monohydrate and PAA is completed using the flow of the incoming PAA solution. The PAA solution is dissolved with the citric acid monohydrate to lower the pH of the final solution to between about 5.0 and about 6.0, for example, 6.0.

In an embodiment, the acidified peracetic acid solution is removed from second reactor chamber 26 through filter or mesh 22b, which filters any undissolved solids from the acidified peracetic acid solution, at a flow rate, such as from about 4.5-6.1 liters per minute (1.2-1.6 gallons per minute), for example, about 5.3 liters per minute (1.4 gallons per minute) and at a temperature of about 50-65° C. The acidified peracetic acid solution is transferred to storage reservoir or chamber 50, in one embodiment, storage reservoir of chamber 50 comprises about 4-12 liters of the high level disinfectant solution having a temperature of about 30-55° C. with a concentration of PAA from about 1200-2200 ppm, more specifically, about 1200-2000 ppm, a hydrogen peroxide concentration of less than 500 ppm, more specifically less than 300 ppm, and a pH of from about 5.0-7.0. For example, 4 liters of a final disinfectant solution may have a concentration of about 1200-2200 ppm, more specifically, about 1200-2000 ppm, and more specifically about 1700-1900 ppm PAA, with a pH of about 6.

Another representative embodiment is a method for using continuous flow system 60 to make a high level disinfectant solution. The method includes dispensing the solid components into their respective chambers, allowing the water source to reach the desired temperature, turning on the pump 32, and allowing the flow of liquid from the water source 30 to the first reactor chamber 24, to the second reactor chamber 26 and to the storage reservoir or chamber 50.

The continuous flow system 60 is advantageous because it does not require additional motors or parts for mixing, it allows production of the high level disinfectant solution in large quantities with no requirement for larger vessels, and no pressure check valves are required.

Such a system has advantages that include requiring less total solids, a system that is easy to clean, a fast running time, and the ability of the system to generate its own heated water.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure in intended to embrace all such alternatives, modifications, and variations as fall within the scope of the claims, together with all equivalents thereof.

The invention claimed is:

1. An apparatus to make a peracetic acid high level disinfectant solution comprising:
   a) a solid dispensing system comprising a bulk dispenser for a solid mixture of TAED, a bulk dispenser for a solid mixture of sodium percarbonate, and a bulk dispenser for solid citric acid monohydrate,
   b) a heated water delivery system,
   c) a first reactor chamber to mix solid TAED and solid sodium percarbonate with heated water to provide a first peracetic acid solution,
   d) a first conduit to deliver heated water from the heated water system to the first reactor chamber,
   e) a second reactor chamber to mix the first peracetic acid solution with solid citric acid monohydrate to provide a pH controlled peracetic acid solution,
   f) a second conduit to deliver the peracetic acid solution from the first reactor chamber to the second reactor chamber,
   g) a storage reservoir to dilute the pH controlled peracetic acid solution with water to provide the peracetic acid high level disinfectant solution,
   h) a third conduit to deliver the pH controlled peracetic acid from the second reactor chamber to the reservoir, and
   i) a fourth conduit to deliver water to the storage reservoir.

2. The apparatus of claim 1 wherein the heated water delivery system comprises a pump to deliver heated water to the first reactor chamber.

3. The apparatus of claim 1 wherein the heated water delivery system delivers water to the first reactor chamber at a temperature of about 40° C.

4. The apparatus of claim 1 wherein the first reactor chamber comprises a rotary mixing blade.

5. The apparatus of claim 1 wherein the first reactor chamber mixes the water, the solid TAED and the solid sodium percarbonate for about 1 minute.

6. The apparatus of claim 1 wherein the second conduit to deliver peracetic acid solution to the second reactor chamber includes a first filter to prevent transfer of undissolved solids.

7. The apparatus of claim 1 wherein the third conduit to deliver pH controlled peracetic acid to the storage reservoir includes a second filter to prevent transfer of undissolved solids.

8. The apparatus of claim 1 wherein the water to dilute the pH controlled peracetic acid is delivered to the storage reservoir at a temperature in the range of about 18 to about 40° C.

9. The apparatus of claim 1 wherein the peracetic acid high level disinfectant solution is at a temperature greater than about 25° C., has a pH in the range of between about 5 and about 7, a peracetic acid concentration of about 1200-2200 ppm, and a hydrogen peroxide concentration of less than about 300 ppm.

10. A method of making a peracetic acid high level disinfectant solution comprising the steps of:
   a) dispensing a solid TAED from a first bulk container into a first reactor chamber,
   b) dispensing a solid sodium percarbonate from a second bulk container into the first reactor chamber,
   c) adding heated water to the first reactor chamber,
   d) mixing the heated water, TAED and sodium percarbonate to form a peracetic acid solution,
   e) dispensing solid citric acid monohydrate from a third bulk container into a second reactor chamber,
   f) adding the peracetic acid solution to the second reactor chamber to provide a pH controlled peracetic acid solution,
   g) adding the pH controlled solution to a storage reservoir, and
   h) diluting the pH controlled peracetic acid solution with water to provide the peracetic acid high level disinfectant solution.

11. The method of claim 10 wherein the heated water is pumped into the first reactor chamber.

12. The method of claim 10 wherein the heated water is at a temperature of about 40° C.

13. The method of claim 10 wherein the heated water, solid TAED and solid sodium percarbonate are mixed in the first reactor chamber by a rotary mixing blade.

14. The method of claim 10 wherein the heated water, solid TAED and solid sodium percarbonate are mixed in the first reactor chamber for about 1 minute.

15. The method of claim 10 wherein the peracetic acid solution is pumped into the second reactor chamber.

16. The method of claim 10 wherein the peracetic acid solution is filtered to prevent transfer of undissolved solids into the second reactor chamber.

17. The method of claim 10 wherein the pH controlled peracetic acid is filtered to prevent transfer of undissolved solids into the storage reservoir.

18. The method of claim 10 wherein the water to dilute the pH controlled peracetic acid is at a temperature in the range of about 18 to about 40° C.

19. The method of claim 10 wherein the peracetic acid high level disinfectant solution is at a temperature of about 30° C., has a pH in the range of about 5 and about 7, a peracetic acid concentration of about 1200-2200 ppm, and a hydrogen peroxide concentration of less than about 300 ppm.

* * * * *